United States Patent [19]

Ryu

[11] 4,119,675

[45] Oct. 10, 1978

[54] PROCESS FOR TRANSALKYLATION OF ALKYLAROMATIC HYDROCARBONS USING A CATALYST COMPRISING TiF$_4$ AND A METAL OXIDE

[75] Inventor: Ji-Yong Ryu, Des Plaines, Ill.

[73] Assignee: UOP Inc., Des Plaines, Ill.

[21] Appl. No.: 789,581

[22] Filed: Apr. 21, 1977

Related U.S. Application Data

[62] Division of Ser. No. 644,786, Dec. 29, 1975, Pat. No. 4,048,248.

[51] Int. Cl.$^2$ ............................ C07C 3/62; C07C 5/28
[52] U.S. Cl. ............................. 260/672 T; 260/668 A
[58] Field of Search ........................ 260/672 T, 668 A

[56] References Cited

U.S. PATENT DOCUMENTS

| | | | |
|---|---|---|---|
| 2,683,758 | 7/1954 | McCaulay et al. | 260/672 T |
| 2,683,759 | 7/1954 | McCaulay et al. | 260/672 T |
| 2,683,760 | 7/1954 | McCaulay et al. | 260/672 T |
| 2,683,761 | 7/1954 | McCaulay et al. | 260/672 T |
| 2,834,821 | 5/1958 | Bergsteinsson | 260/672 T |
| 2,999,074 | 9/1961 | Bloch et al. | 252/441 |
| 3,354,078 | 11/1967 | Miale et al. | 260/672 T |
| 3,637,881 | 1/1972 | Williams et al. | 260/668 A |
| 3,720,726 | 3/1973 | Mitsche et al. | 260/672 T |

FOREIGN PATENT DOCUMENTS 1,044,490  9/1966  United Kingdom ............... 260/672 T Primary Examiner—Delbert E. Gantz
Assistant Examiner—C. E. Spresser
Attorney, Agent, or Firm—James R. Hoatson, Jr.; John G. Cutts, Jr.; William H. Page, II

[57] ABSTRACT

Process for the conversion of aromatic hydrocarbons. Especially useful for reaction of an alkylating agent, preferably propylene, with an aromatic hydrocarbon. Novel feature is use of a catalyst system comprising TiF$_4$ and a metal oxide which possesses surface hydroxyl groups.

8 Claims, No Drawings

PROCESS FOR TRANSALKYLATION OF ALKYLAROMATIC HYDROCARBONS USING A CATALYST COMPRISING TIF₄ AND A METAL OXIDE

CROSS REFERENCE TO RELATED APPLICATION

This application is a division of my prior, copending application Ser. No. 644,786 filed Dec. 29, 1975, now U.S. Pat. No. 4,048,248, Sept. 13, 1977.

BACKGROUND OF THE INVENTION

1. Field of the Invention

The present invention relates to an improved process for the conversion of an aromatic hydrocarbon in the presence of a titanium tetrafluoride catalyst system. The invention will be described with reference to alkylation, e.g., the synthesis of cumene by alkylation of benzene with propylene in the presence of the catalyst. The invention may also be used for alkylaromatic transalkylation and isomerization.

2. Description of the Prior Art

Conversion of aromatic hydrocarbons is well known in industry. Some of the aromatic conversion reactions which occur include alkylation of aromatic hydrocarbons with an alkylating agent such as an olefin, disproportionation or transalkylation of alkylaromatic hydrocarbons and isomerization of alkylaromatic hydrocarbons such as xylenes, and of dialkyl and higher substituted aromatics.

Of special interest, has been the propylation of benzene to cumene. Cumene is used for the production of phenol and acetone. Cumene is also dehydrogenated to form methylstyrene, in a process similar to that used to convert ethylbenzene to styrene. Cumene is also used as a blending component in aviation gasoline because of its high octane number. The consumption of cumene in the U.S.A. was about 350,000 metric tons in 1968. Of this total, 94% was used for the production of phenol or acetone.

It is well known that cumene can be synthesized from benzene and propylene using a catalyst of AlCl₃, SPA or BF₃. SPA is a generally accepted abbreviation for solid phosphoric acid catalyst, or phosphoric acid which is adsorbed on kieselguhr or other support.

AlCl₃ is a very popular alkylation catalyst, because of its high activity. Unfortunately, the catalyst operates as a slurry or sludge which is messy to handle on a commercial scale, and also is corrosive. The highly reactive nature of this Friedel-Crafts metal halide catalyst, AlCl₃, is desirable when attempting to alkylate benzene with ethylene, because less active catalyst systems do not work. However, for alkylation with propylene such highly reactive systems are not necessary.

Another highly selective catalyst system has been developed for the alkylation of benzene with olefins. This catalyst comprises boron trifluoride. The boron trifluoride catalyst system is exceptionally active and permits operation with dilute olefin streams, but it requires the continuous addition of BF₃ to maintain catalyst activity. High catalyst activity also leads to oligomerization of olefins so contact time of olefins with BF₃ catalyst should be as short as possible. This catalyst is also exceptionally water sensitive, as water not only destroys the catalyst, but produces very corrosive solutions which attack downstream processing units. BF₃ also frequently appears in the product and must be removed therefrom.

Because of the interest in alkylating benzene with propylene to make cumene, and because of the inadequacies of existing catalyst systems, I studied the work that others had done, and made exhaustive investigations to determine if it would be possible to find a catalyst which would have the activity and selectivity required to produce an acceptable cumene product, while making maximum use of existing petroleum resources and provide an improved process for the manufacture of cumene.

A highly active catalyst was sought to operate with less catalyst and to reduce operating or construction cost. In new units this would mean smaller, and cheaper reactor vessels, while in existing units it would mean that an increase in capacity could be obtained merely by changing catalyst in an existing reactor vessel with only minor modifications of the plant.

High selectivity is necessary, not only to permit operation with feedstreams which are not 100% pure propylene, but also to maximize production of the desired cumene product, and to minimize production of polymerized olefins, or polyalkylated aromatic compounds.

Accordingly, many catalyst systems were studied to find a catalyst with excellent activity and selectivity, which was not corrosive or destroyed by water.

There has been extensive work done with Ti catalysts, thought most work occurred in conjunction with studies of Ziegler-Natta catalysts. The closest prior art known is U.S. Pat. Nos. 2,381,481 (Class 260-683.15), 2,951,885 (Class 260-671), 2,965,686 (Class 260-671) and 3,153,634 (Class 252-429).

In U.S. Pat. No. 2,381,481, preparation and use of a catalyst prepared by treating alumina gel with fluotitanic acid is disclosed. This catalyst is used for polymerization of olefins to heavier hydrocarbons, and also for alkylation of paraffins with olefins, the latter when operating at high temperatures, between 700° and 900° F. or higher. No mention is made of alkylation of aromatics with olefinic hydrocarbons.

In U.S. Pat. No. 2,951,885, there is disclosed the use of titanium trihalide on activated alumina or other activated acidic oxide for alkylation of benzene with olefins. The catalyst is originally a tetrachloride, subsequently reduced to the trichloride with an alkali metal such as sodium, lithium, or potassium. The examples show that this catalyst will alkylate benzene with ethylene.

In U.S. Pat. No. 2,965,686, the thrust of the application was to develop a titanium subchloride catalyst. In Example II, a reaction between cumene and propylene was disclosed using titanium tetrachloride catalyst. The catalyst in Example II was not a subfluoride, but rather was a tetrachloride. The reaction occurred for almost three hours at 146° C. in a vessel containing 43 grams of catalyst and 128 grams of cumene. Almost 64% of the cumene was not reacted, while the isopropyl cumene yield was 27.3%, and 2.6% yield of heavier material. It is not certain if the results obtained in this patent are due solely to the use of the tetrachloride, as opposed to the tetrafluoride of applicant's process, or whether the method of preparation of applicant's tetrafluoride also makes a contribution to the improved activity of applicant's catalyst.

In U.S. Pat. No. 3,153,634, there is disclosed the use of titanium subhalides in a polymerization reaction. The patentee is probably describing a form of catalyst to make high molecular weight polymer, as he discusses production of solid polymer products. The patentee in 3,153,634 taught the very antithesis of applicant's reaction. Thus, on page 3 line 65–75, the patentee mentions use of benzene as an inert solvent to hold dissolved olefins, rather than as a reactant.

Accordingly, work continued on developing an improved process for the catalytic conversion of aromatic hydrocarbons.

Accordingly, the present invention provides a process for the catalytic conversion of an aromatic hydrocarbon comprising contacting the aromatic hydrocarbon with a reactant in the presence of a catalyst comprising titanium tetrafluoride composited with a support which contains surface hydroxyl groups and recovering a converted aromatic hydrocarbon as a product of the process.

* * DETAILED DESCRIPTION * *

The catalyst of the present invention comprises a titanium tetrafluoride component, and a support containing surface hydroxyl groups, e.g., a Group III-A metal oxide. Use of titanium tetrafluoride alone, e.g., dispersed on an inert, high surface area support, such as silica, does not produce an active catalyst. It is only with the use of metal oxide possessing surface hydroxyl groups that the titanium tetrafluoride catalyst system produces satisfactory activity.

One of the best supports is alumina, especially gamma-alumina. The alumina preferably has a bulk density of 0.3 to 0.7 g/cm$^3$ and a surface area of 1 to 500 m$^2$/g. It would also be possible to disperse the catalyst system of the present invention on an inert support and still have an active catalyst. Thus, titanium tetrachloride and gamma-alumina could be impregnated on a ceramic honeycomb, available as an article of commerce with the Dow-Corning Corporation. Use of titanium tetrafluoride alone on such a ceramic support would not produce an active catalyst. Other preferred Group III-A metal oxides which may be used include the oxides of gallium, indium, and thallium.

If the catalyst system is supported on an inert, carrier, any of the well known supports can be used. These include silica, clays, charcoal, gravel, sand, etc., though all of these will not give equivalent results.

It is also within the scope of the present invention to add one or more promoters to the catalyst system. It is believed that promoters from Group III and Group VI-B may be beneficial.

When it is desired to use the catalyst system in an alkylaromatic isomerization process, then alkylaromatic isomerization reaction conditions should be used. Reaction conditions are disclosed in U.S. Pat. No. 3,637,881 (Class 260-668 *a*), the teachings of which are incorporated by reference. When it is desired to use the catalyst system of the present invention for alkylaromatic transalkylation then appropriate reaction conditions should also be used. These are disclosed in U.S. Pat. No. 3,720,726 (Class 260-672 *t*), the teachings of which are incorporated by reference. Reaction conditions for the alkylation of aromatic hydrocarbons will be discussed in detail in a latter part of this specification.

Two different catalyst preparation techniques have been used, sublimation and impregnation.

In one sublimation procedure titanium tetrafluoride may be placed on top of a bed of gamma-alumina. Preferably the support is predried at 300° to 600° C. for 1 to 10 hours under hydrogen or an inert gas flow to activate the alumina and remove all water and water-forming compounds therefrom. Drying at higher temperatures depletes the alumina of hydroxyl groups and should be avoided. Non predried, commercial alumina may also be used but there will be a significant loss of TiF$_4$ to titanium oxide or titanium oxyfluoride. The titanium tetrafluoride and alumina should be maintained in a dry, inert atmosphere, after drying. While passing nitrogen downflow over the mixture of alumina and titanium tetrafluoride, the temperature is slowly increased to a temperature slightly above the sublimation temperature of titanium tetrafluoride, then the temperature is progressively increased to elevated temperatures. This thermal pretreatment step is preferably 250° to 350° C. for ½ to 2 hours, followed by treatment at 400° to 600° C. for 1 to 10 hours.

Another way to prepare catalyst for use in the present invention is to impregnate the Group III-A metal oxide with a solution containing a compound which will decompose to form titanium tetrafluoride upon heating in an inert atmosphere while not converting TiF$_4$ to lower valence Ti compound. A preferred titanium tetrafluoride impregnating solution consists of an organic or aqueous solution of TiF$_4$ or an aqueous solution of M$_2$TiF$_6$, where M equals H, Li, Na, or K. In all impregnating methods it is preferred to contact the metal oxide with impregnating solution at room temperature and then progressively increase the temperature to evaporate the solution. The catalyst is then preferably thermally treated at 100° to 200° C. for ½ to 2 hours and then at 250° to 350° C. for ½ to 2 hours and then at 400° to 600° C. for 1 to 10 hours under an inert atmosphere.

Unfortunately, the sublimation procedure requires excess amounts of titanium compounds to insure that all parts of the Group III-A metal oxide are contacted by titanium compounds. Because of the difficulties encountered with this procedure, the impregnation of the titanium compounds onto the Group III-A metal oxide is much preferred. In impregnation, it is of course possible to vary over a wide range the concentration of titanium compound in the finished catalyst system. A preliminary evaluation of the optimum amount of titanium tetrafluoride indicates that about the same amount of titanium should be added via the impregnation procedure as would be incorporated using a sublimation procedure. Adding more titanium than this does not seem to produce significantly increased catalytic activity, while having less titanium than this optimum amount impairs catalytic activity. At least about 0.5 weight percent titanium is believed necessary for a significant amount of reaction to occur. The upper limit on titanium is about 20 wt. %.

The ratios of reactants and other reaction conditions which occur when alkylating benzene with propylene are basically those well known in the art. Pressures may range from 1 to 100 atmospheres, or even higher. It is desirable to maintain pressures high enough to have a liquid phase in the reaction zone. Although it is possible to operate at very high pressure, little advantage is gained thereby, in fact, an increase in pressure seems to have a harmful effect. High pressure does not seem to effect the selectivity of the reaction to produce cumene, but rather seems to encourage the formation of non-aromatic compounds, possibly propylene trimers. Thus, operation at pressure above around 500 atm leads to the production of trace amounts of non-aromatic compounds, as determined by gas chromotography. Operation at pressures lower than 50 atm eliminated these.

Preferred pressure seems to be around 20 to 60 atm, with an optimum pressure of about 35 atm.

Temperature effects both the conversion and selectivity of the reaction. Temperature may range between ambient and 250° C. At very low temperatures, the catalyst is not sufficiently active to permit the desired reaction to proceed at a satisfactory rate. At very high temperatures, it is believed that the catalyst may be damaged, either by stripping away of the titanium tetrafluoride component, or by formation of carbonaceous materials on the catalyst.

If the reaction is kinetically controlled, an increase in temperature should increase the rate of reaction. As a general statement, this is true, but the temperature dependence is not as large as expected, so the reaction may be limited by mass transport of reactants and products to and from the catalyst surface. Preferred operating temperatures seem to be about 100° to 200° C. It was difficult to pick an optimum temperature, but this may be because conversion of olefins was so high. Further studies, with less conversion, may indicate an optimum temperature for this reaction.

The catalyst may be disposed in a reactor vessel as a fixed, fluidized or moving bed of catalyst. The reactants may contact the catalyst in upflow, downflow or crossflow fashion, though upflow of reactants over a fixed bed of catalyst is preferred.

The liquid hourly space velocity in the reactor may range from 0.1 to 20. However, higher LHSV is possible depending on the desired conversion level of propylene. Because catalyst of the present invention is very active for the alkylation reaction, significantly higher space velocities are possible then when using some prior art catalysts, e.g., SPA. To some extent, the liquid hourly space velocity is related to temperature in the reaction zone, in general, a higher LHSV will require higher temperature operation.

As used herein, conversion refers to the disappearance of reactants. Thus, conversion refers to percent disappearance of propylene feed. Selectivity means the amount of cumene produced per mole of propylene that was consumed, expressed as percent. Thus 90% conversion means that for every 100 moles of propylene entering the reactor, 90 moles were converted to something else. A selectivity of 80% would mean that 72 moles of cumene were formed, e.g., that 80% of the 90 moles of propylene consumed were converted to cumene.

EXAMPLE I

This example shows how to make a catalyst via a sublimation technique. About 200 ml of gamma-alumina in the form of 1.6 mm spheres, prepared by the well known oil drop method, was dried at 550° C. for 300 minutes under $H_2$ flow. The apparent bulk density was 0.52 g/cc. The $H_2$ flow was replaced with $N_2$ flow and the alumina cooled to room temperature. About 30 grams of $TiF_4$ was placed on top of the predried alumina. Temperature was slowly increased to 310° C. while maintaining a downflow of $N_2$ over the alumina. This temperature was maintained for 90 minutes. Temperature was then increased to 350° C. for 15 minutes, then to 400° C. for 30 minutes.

EXAMPLE II

This example shows how to make an impregnated catalyst of the present invention. Gamma-alumina was impregnated with aqueous $TiF_4$, solution. The solution was prepared by dissolving $H_2TiF_6$ in deionized water. The alumina and impregnating solution were cold rolled in a rotating steam drier, then steam was turned on to evaporate the solution. These catalysts were then given further thermal treatments under $N_2$ flow. In one instance, a Cr promoter was added to the catalyst by dissolving $CrO_3$ in the impregnating solution. Details of the preparation of these catalysts are shown in Table I. These were catalysts A, B and C.

TABLE I

| Catalyst | IMPREGNATION | | | | | THERMAL TREATMENT (All With 2000 cc/min $N_2$ Flow) | | | |
|---|---|---|---|---|---|---|---|---|---|
| | Alumina cc | 60% $H_2TiF_6$ g | Impreg. Solution cc | Volume cc | Cold Roll minutes | First °C/hours | Second °C/hours | Third °C/hours | Fourth °C/hours |
| A | 200 | 12.44 | 7.55 | 250 | 60 | 150/1 | 200/1.25 | 300/1 | 500/5 |
| B | 125 | 6.0 | 4.0 | 125 | 30 | 150/1 | 200/1 | 300/1 | 350/3.25 |
| C | 300 | 16.5 | 10.0 | 300 | 30 | 140/1 | 300/1.5 | 500/3 | — |

Note:
Catalyst A also contained Cr added by dissolving 5.15 g CrO to the impregnating solution

EXAMPLE III

In this instance a commercially available solid phosphoric acid catalyst was used for comparison purposes. This was catalyst D.

EXAMPLE IV

The catalysts were tested in a laboratory scale plant. The reaction studied was alkylation of benzene with propylene. Catalyst was maintained as a fixed bed, of 50 cc volume. The reactants were passed upflow over the catalyst bed. Benzene was dried by circulating it over high surface area sodium. Pure propylene was dried by passing it over type 4-A molecular sieves. Benzene and propylene were mixed together and then charged to the reactor. The reactions were all carried out at 120° to 245° C., 1 to 3 LHSV, and at 25 to 55 atmospheres pressure. The reactor was started up full of liquid benzene and then the mixture of propylene and benzene added. It is believed that if propylene alone is charged, or even propylene and benzene charged simultaneously, high molecular weight polymer may form.

Reaction conditions and test results are reported in Table II. Conversion (C) refers to conversion of propylene in the feed, while selectivity (S) refers to moles of cumene produced per mole of propylene reacted, expressed as mole percent. Productivity (P) refers to weight percent cumene in product.

TABLE II

| | SUMMARY OF RESULT | | | | | | | |
|---|---|---|---|---|---|---|---|---|
| | Reaction Condition | | | | Hrs. on | | | |
| Catalyst | T (° C) | P (atm) | Bz/C$_3$ | LHSV | Stream | C | S | P |
| B | 120 | 55 | 6.24 | 1.1 | 17–22 | 72.1 | 59.2 | 69.1 |

TABLE II-continued
SUMMARY OF RESULT

| Catalyst | T (°C) | P (atm) | Bz/C | LHSV | Hrs. on Stream | C | S | P |
|---|---|---|---|---|---|---|---|---|
| B | 120 | 55 | 6.10 | 2.1 | 38-43 | 52.1 | 63.3 | 75.0 |
| B | 150 | 55 | 6.00 | 2.0 | 58-63 | 80.3 | 62.3 | 72.4 |
| B | 150 | 55 | 5.5 | 1.1 | 78-83 | 86.0 | 57.6 | 67.2 |
| B | 120 | 55 | 6.6 | 2.0 | 96-101 | 48.4 | 67.3 | 78.1 |
| B | 150 | 35 | 4.6 | 0.9 | 116-121 | 84.2 | 57.5 | 67.4 |
| B | 150 | 35 | 5.3 | 2.1 | 136-141 | 73.1 | 56.7 | 67.0 |
| B | 150 | 28 | 5.0 | 2.2 | 156-161 | 75.1 | 58.7 | 68.4 |
| B | 150 | 28 | 5.1 | 0.9 | 178-182 | 84.8 | 48.7 | 61.1 |
| B | 150 | 55 | 7.5 | 2.0 | 195-199 | 78.6 | 74.6 | 77.2 |
| B | 150 | 55 | 9.0 | 3.1 | 215-219 | 80.1 | 62.2 | 71.4 |
| B | 150 | 35 | 8.1 | 3.1 | 229-233 | 79.1 | 71.9 | 79.5 |
| B | 150 | 35 | 7.8 | 2.0 | 245-249 | 90.0 | 70.4 | 78.2 |
| B | 120 | 55 | 5.3 | 2.1 | 266-270 | 81.1 | 63.7 | 74.9 |
| B | 180 | 35 | 8.1 | 2.1 | 279-283 | 92.0 | 67.4 | 75.7 |
| B | 180 | 35 | 4.9 | 2.1 | 299-303 | 90.0 | 56.8 | 66.8 |
| D | 180 | 35 | 8.6 | 1.0 | 14-18 | 81.6 | 84.5 | 89.1 |
| D | 180 | 35 | 7.9 | 2.0 | 35-39 | 75.5 | 87.8 | 91.5 |
| D | 180 | 35 | 5.39 | 1.1 | 44-48 | 83.1 | 83.4 | 88.4 |
| D | 180 | 35 | 4.81 | 0.98 | 64-68 | 84.5 | 84.6 | 89.0 |
| C | 120 | 35 | 4.68 | 1.1 | 13-17 | 95.5 | 62.1 | 71.0 |
| C | 120 | 35 | 4.77 | 2.1 | 25-29 | 95.5 | 61.1 | 70.6 |
| C | 150 | 25 | 5.17 | 2.1 | 41-45 | 93.8 | 61.1 | 70.8 |
| C | 150 | 25 | 5.14 | 2.0 | 45-49 | 93.3 | 58.4 | 68.1 |
| C | 150 | 25 | 4.95 | 1.1 | 61-65 | 96.5 | 57.7 | 67.4 |
| C | 150 | 25 | 4.84 | 2.9 | 77-81 | 81.7 | 61.7 | 71.0 |
| C | 150 | 25 | 8.59 | 2.1 | 89-93 | 92.8 | 71.5 | 78.8 |
| C | 150 | 25 | 7.85 | 2.0 | 93-97 | 93.0 | 69.6 | 77.6 |
| C | 150 | 25 | 7.48 | 1.0 | 105-109 | 93.7 | 73.8 | 81.1 |
| C | 150 | 25 | 6.87 | 1.0 | 109-113 | 93.8 | 67.8 | 76.3 |
| C | 150 | 25 | 2.86 | 1.1 | 125-129 | 97.9 | 48.5 | 59.3 |
| C | 150 | 25 | 2.88 | 2.3 | 141-145 | 96.6 | 46.7 | 57.5 |
| C | 150 | 35 | 3.07 | 2.3 | 157-161 | 95.6 | 49.9 | 60.5 |
| C | 150 | 35 | 3.06 | 1.2 | 173-177 | 94.6 | 50.0 | 60.6 |
| C | 150 | 35 | 5.03 | 1.0 | 189-193 | 95.0 | 60.7 | 70.0 |
| C | 150 | 35 | 5.08 | 2.0 | 197-201 | 96.6 | 65.0 | 71.9 |
| C | 150 | 35 | 4.94 | 2.0 | 205-109 | 96.0 | 61.7 | 70.8 |
| C | 150 | 25 | 4.92 | 3.0 | 217-221 | 96.0 | 64.4 | 68.8 |
| C | 150 | 35 | 8.11 | 2.1 | 233-237 | 89.8 | 80.3 | 78.8 |
| C | 150 | 35 | 8.10 | 2.0 | 237-241 | 95.5 | 65.7 | 72.2 |
| C | 150 | 35 | 7.35 | 1.0 | 249-253 | 92.4 | 78.7 | 80.1 |
| C | 120 | 25 | 5.20 | 2.1 | 265-269 | 96.3 | 60.6 | 70.2 |
| C | 120 | 25 | 4.94 | 2.0 | 269-273 | 96.1 | 57.7 | 67.3 |
| C | 120 | 25 | 5.18 | 3.0 | 281-285 | 91.8 | 61.7 | 71.2 |
| C | 120 | 25 | 4.93 | 3.0 | 285-289 | 95.5 | 56.9 | 69.4 |
| C | 120 | 25 | 7.55 | 2.0 | 301-305 | 93.2 | 75.6 | 82.9 |
| C | 120 | 25 | 7.69 | 3.0 | 317-321 | 94.7 | 74.6 | 81.4 |
| C | 120 | 25 | 2.82 | 3.5 | 325-329 | 96.4 | 49.3 | 58.5 |
| C | 120 | 25 | 2.76 | 2.1 | 349-353 | 95.2 | 47.2 | 58.2 |
| C | 120 | 25 | 4.91 | 1.9 | 357-361 | 94.7 | 57.8 | 67.8 |
| C | 120 | 25 | 4.82 | 1.9 | 361-365 | 96.3 | 63.1 | 70.2 |
| C | 120 | 25 | 4.95 | 3.0 | 373-377 | 93.0 | 60.7 | 70.3 |
| C | 120 | 25 | 5.27 | 3.2 | 377-381 | 91.6 | 59.8 | 69.5 |

Because of poor weight recoveries experienced when testing catalyst A, the results obtained with catalyst A are not recorded in Table II. However, the products obtained were analyzed, and it is believed that the analysis of products gives a good indication of the catalyst system's performance. Table III provides a comparison of the product streams produced by the different titanium tetrafluoride catalysts. From these data it can be observed that the catalyst containing chromium promoter is very selective for the production of cumene.

TABLE III
Comparison of Various Supported Titanium Tetrafluoride Catalysts.

| CATALYST | A | | | | C | | B | |
|---|---|---|---|---|---|---|---|---|
| Hours of Operation | 10 | 20 | 40 | 70 | 190 | 200 | 140 | 300 |
| *Light Ends | 0.2 | 0.3 | 0.4 | 0.4 | 0.1 | 0.1 | 1.7 | 0.7 |
| Benzene | 72.5 | 73.0 | 56.5 | 55.5 | 74.2 | 77.8 | 79.2 | 77.0 |
| Toluene | Tr | Tr | Tr | Tr | | | | |
| Ethylbenzene | 0.1 | Tr | 0.1 | 0.1 | | | | |
| Cumene | 23.7 | 20.2 | 33.4 | 32.9 | 18.0 | 15.9 | 12.8 | 14.9 |
| n-Propylbenzene | 0.1 | Tr | 0.1 | 0.1 | | | | |
| Unknowns | 0.1 | Tr | 0.1 | 0.1 | | | 0.1 | |
| 1.4-Dimethyl-2-Ethylbenzene | 2.0 | 3.0 | 5.6 | 6.1 | | | | |
| Unknowns | 1.3 | 3.5 | 3.8 | 4.8 | | | | |
| Dipropylbenzene | | | | | 6.7 | 5.0 | 5.1 | 6.3 |
| Tripropylbenzene | | | | | 1.0 | 1.2 | 1.1 | 1.1 |
| **$C_9$— | | | 93.8 | 88.9 | 88.4 | | | |
| Unknowns | | | | 0.1 | 0.1 | | | |
| $C_{12}$ Aromatics | | | 5.6 | 9.9 | 10.4 | | | |
| Unknowns | | | | 0.2 | 0.1 | | | |
| $C_{15}$ Aromatics | | | 0.5 | 0.5 | 0.6 | | | |
| Unknowns | | | | 0.2 | 0.2 | | | |
| $C_{18}$ Aromatics | | | 0.1 | 0.1 | 0.1 | | | |
| Heavies | | | Tr | 0.1 | 0.1 | | | |
| Re- T (°C) | 180 | 180 | 245 | 245 | 150 | 150 | 150 | 180 |

TABLE III-continued

| | | Comparison of Various Supported Titanium Tetrafluoride Catalysts. | | | | | | |
|---|---|---|---|---|---|---|---|---|
| CATALYST | | A | | | | C | | B |
| Re- | P (atm) | 55 | 55 | 55 | 55 | 35 | 35 | 35 | 35 |
| action Condi- | $C_6H_6/C_3H_6$ | 4.5 | 4.9 | 2.6 | 2.6 | 5.0 | 5.1 | 5.3 | 4.9 |
| tion | LHSV | 1.8 | 2.0 | 4.2 | 4.2 | 1.0 | 2.0 | 2.1 | 2.1 |

*by gas chromatography
**by boiling point

Based on these studies it is believed that the important factor in the thermal treating steps is the temperature, rather than the total time, as long as the total period for thermal treatment is reasonably long, around 5 or 6 hours. It is believed that the activity of the catalyst is effected by the thermal treatment temperatures because the desorption of water molecules from the catalyst surface may require higher temperature than certain initial temperatures. Water can compete for active sites with the reactants, thus water is to some extent a catalyst poison. However, if catalyst deactivation occurs due to water adsorption, the catalyst can be regenerated by appropriate further thermal treatment under inert gas flow. Any regenerative thermal treatments should probably approximate those of the original thermal treatments, in that heating which is too rapid, or too high a temperature, may cause hydrolysis of the $TiF_4$ component on the catalyst, which would reduce catalyst activity. Another danger of a rapid high temperature catalyst regeneration would be the formation of corrosive gases and liquids due to rapid evolution of $H_2O$ vapor and fluorine compounds.

Although water is discussed above as a catalyst poison, the titanium tetrafluoride catalyst system of the present invention is much less susceptible to attack by water than are corresponding titanium tetrachloride catalysts. For some reason, not yet fully understood, the fluoride is held much more tenaciously by the support than the corresponding chloride compounds.

The catalyst which contained a chromium compound in addition to $TiF_4$ showed superior selectivity to cumene when compared to non-promoted $TiF_4$ catalysts. From the data it may be seen that all of the catalysts of the present invention are at least 2 to 3 times as active as SPA catalysts. With the addition of Cr promoter, the catalyst system of the present invention has almost the same selectivity to cumene as SPA catalyst. It is not understood why the addition of Cr promoter is beneficial. The reaction may be more selective, but it is also possible that a certain amount of transalkylation also occurs. Although the selectivities to cumene of Ti catalyst were slightly lower than that of SPA, since these catalysts were able to transalkylate, it is possible to carry out the reaction with low benzene/$C_3H_6$ mole ratio feeds by reintroducing polyalkylated benzene into the reactor or installing a separate reactor for transalkylation to produce high purity cumene product.

From the data it is also apparent that increasing the benzene to propylene ratio increases the selectivity of the reaction for cumene. This phenomenon was expected, and is typical of prior art processes using SPA or $BF_3$ catalysts.

The catalyst of the present invention is also believed more stable than prior art catalyst. The stability of a catalyst is technically very important. Ti fluoride is very stable compared with the titanium chloride (due to the lower value of heat of formation of fluoride than that of titanium chloride). My titanium catalyst is reasonably stable to air. A high water content in the feed or too long exposure to air will reduce catalyst activity. However, it is possible to restore the catalyst activity by simply passing dry inert gas on the catalyst at elevated temperatures.

Thus, it can be seen that the process of the present invention provides a viable alternative to existing catalyst systems. The process of the present invention permits operation at lower temperatures if desired, and with increased throughputs, while using a catalyst which is less corrosive and easier to handle than some prior catalyst systems.

I claim as my invention:

1. A process for the transalkylation of an alkylaromatic hydrocarbon which comprises contacting the alkylaromatic hydrocarbon at transalkylation conditions with a catalyst consisting essentially of titanium tetrafluoride and a Group III-A metal oxide which contains surface hydroxyl groups, and recovering a transalkylated hydrocarbon as a product of the process.

2. The process of claim 1 wherein the catalyst is prepared by impregnating the metal oxide with $TiF_4$, and drying in an inert atmosphere at 200° to 600° C.

3. The process of claim 2 wherein the impregnating solution used is selected from the group of an aqueous solution of $TiF_4$, polar organic solvent solutions of $TiF_4$ and aqueous solutions of $M_2TiF_6$ where M is H, Li, Na, or K.

4. The process of claim 1 wherein the catalyst is prepared by subliming $TiF_4$ in a carrier gas and contacting the gas and $TiF_4$ with the metal oxide at a temperature of 284° to 700° C.

5. The process of claim 1 wherein the catalyst is given a thermal pre-treatment at 100° to 200° C. for ½ to 2 hours, then at 250° to 350° C. for ½ to 2 hours, and then at 400° to 600° C. for 1 to 10 hours.

6. The process of claim 1 wherein the metal oxide has an apparent bulk density of 0.3 to 0.8 gm/cm³ and a surface area of 1 to 500 m²/g.

7. The process of claim 1 wherein the Group III-A metal oxide is selected from the group of oxides of aluminum, thallium, gallium and indium.

8. The process of claim 1 wherein the catalyst contains, on an elemental basis, about 0.5 to 20 weight percent titanium.

* * * * *